United States Patent
Cheong et al.

(10) Patent No.: US 7,429,744 B2
(45) Date of Patent: *Sep. 30, 2008

(54) REDUCED COST AND COMPLEXITY MEDIA RECOGNITION SYSTEM WITH SPECULAR INTENSITY LIGHT DETECTOR

(75) Inventors: Jiin Cheang Cheong, Penang (MY); Boon Keat Tan, Penang (MY); Saiful Bahari Saidan, Amapang (MY); Sze Yin Lee, Penang (MY)

(73) Assignee: Avago Technologies General IP (Singapore) Pte Ltd, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 11/789,555

(22) Filed: Apr. 24, 2007

(65) Prior Publication Data

US 2007/0194257 A1      Aug. 23, 2007

Related U.S. Application Data

(63) Continuation of application No. 11/102,411, filed on Apr. 8, 2005, now Pat. No. 7,214,955.

(51) Int. Cl.
 *G01N 21/86* (2006.01)

(52) U.S. Cl. ................................ 250/559.4; 250/221
(58) Field of Classification Search ............. 250/559.4, 250/559.3, 208.1, 221, 235, 214 R; 347/105, 347/106, 14–23
See application file for complete search history.

(56) References Cited

U.S. PATENT DOCUMENTS

| | | | |
|---|---|---|---|
| 5,925,889 A | | 7/1999 | Guillory et al. |
| 6,520,614 B2 * | | 2/2003 | Kaneko ........................ 347/14 |
| 6,561,641 B1 | | 5/2003 | Defosse et al. |
| 6,561,643 B1 | | 5/2003 | Walker et al. |

* cited by examiner

*Primary Examiner*—Que T Le

(57) ABSTRACT

Media type is detected. A light beam is produced. The intensity of a specular reflectance component of the light beam is detected. The specular reflectance component results from the light beam being reflected off media. An indication of detected intensity of the specular reflectance component is compared to a mapping to determine media type of the media. The mapping maps detected intensity of the specular reflectance component to media type. The mapping uses only the detected intensity of the specular reflectance component, and no other components of light, to map detected intensity of the specular reflectance component to media type.

30 Claims, 2 Drawing Sheets

REDUCED COST AND COMPLEXITY MEDIA RECOGNITION SYSTEM WITH SPECULAR INTENSITY LIGHT DETECTOR

CROSS REFERENCE TO RELATED APPLICATIONS

This patent is a continuation of commonly-assigned U.S. patent application Ser. No. 11/102,411, now issued as U.S. Pat. No. 7,214,955, filed on Apr. 8, 2005, titled "Media Recognition Using a Single Light Detector". The content of this patent is incorporated herein by reference for all purposes.

BACKGROUND

When printing with certain types of printers, such as ink jet printers, the type of media can have an effect on print quality. For example, while minimum ink migration may occur when printing on glossy photographic paper, a higher degree of migration will occur when printing on plain paper. Optimizing print on different color media may require different ink mixing. For this reason, many printers control ink volumes and other print characteristics based on media type.

Various media recognition mechanisms have been utilized. For example, many printers allow a user to indicate media type. Based on the media type information provided by the user, the printer can vary print characteristics.

Alternatively, an automated media detection system can be used. For example, a media detect sensor can be used to read an invisible-ink code pre-printed on the media.

Another type of automated media detection system uses a transmitter and two receptors at differing angles with respect to the surface of the media. The two sensors are used to measure, respectively, the specular reflectance of the media and the diffuse reflectance of the media. The ratio of these two reflectance values are analyzed to identify specific media type. Alternatively, a Fourier transform of the to reflective values is used to generate a spatial frequency signature for media. See, for example, U.S. Pat. No. 6,561,643 B1 issued to Walker et al. for Advanced Media Determination System for Inkjet Printing.

SUMMARY

In accordance with an embodiment of the present invention, media type is detected. A light beam is produced. The intensity of a specular reflectance component of the light beam is detected. The specular reflectance component results from the light beam being reflected off media. An indication of detected intensity of the specular reflectance component is compared to a mapping to determine media type of the media. The mapping maps detected intensity of the specular reflectance component to media type. The mapping uses only the detected intensity of the specular reflectance component, and no other components of light, to map detected intensity of the specular reflectance component to media type.

DETAILED DESCRIPTION

Figure 1:
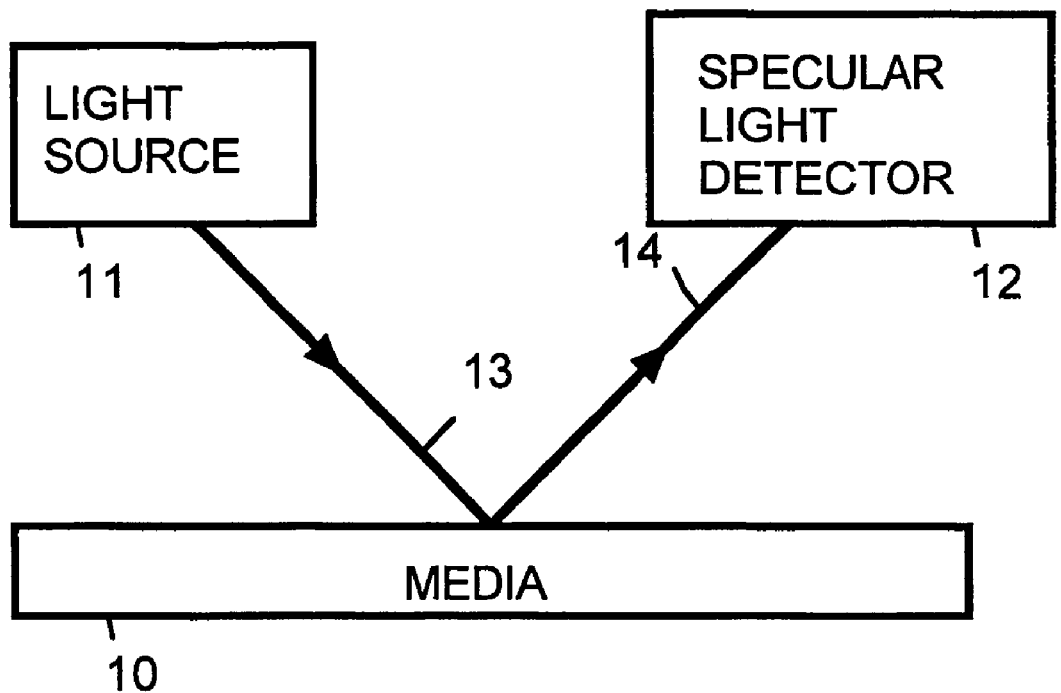
FIG. 1 is a simplified diagram that shows a media recognition system that uses a light source and a single light detector.

FIG. 1 shows a media recognition system that includes a light source 11 and a single light detector 12. For example, the media recognition system is within a system that performs printing, such as a stand-alone printer, a multi-function device, a facsimile machine, or a copier or the media recognition system is within any other device where it is desirable to detect media type and/or presence.

Light source 11 generates a light beam, represented by arrow 13. The light beam is reflected by media 10. A specular reflectance component 14 of the light beam is detected by specular light detector 12. Specular reflectance component 14 is that portion of the light beam that reflects off media 10 at an angle equal to the angle of incidence at which the light beam struck media 10. In addition to producing specular reflectance component 14, when the light beam strikes media 10 some of the light is absorbed by media 10 and some is scattered off the surface of media 10 at angles not equal to the angle of incidence.

Light source 11 is, for example, a light-emitting diode (LED), such as, for example, a blue LED or a blue-violet LED. Alternatively, light source is any other light-emitting device capable of producing specular light reflected from media. Specular light detector 12 is, for example, a photo diode or some other device capable of detecting light intensity.

Figure 2:
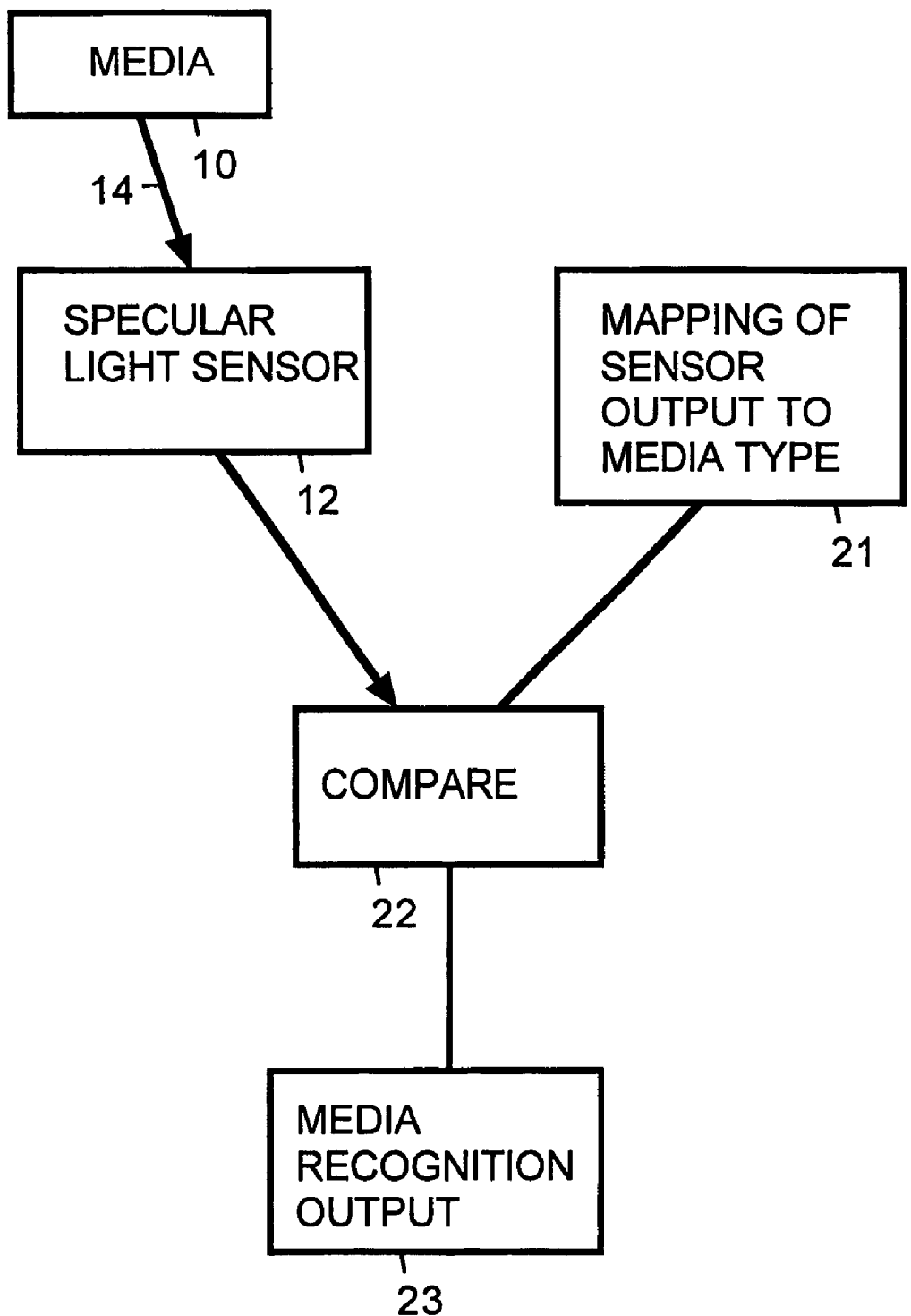
FIG. 2 illustrates operation of the media recognition system shown in FIG. 1.

FIG. 2 shows logical operation of the media recognition system shown in FIG. 1. After detecting specular reflectance component 14, specular light detector 12 forwards to a compare component 22 an indication of the intensity of light within specular reflectance component 14. The indication of the intensity of light within specular reflectance component 14 varies based on the reflectivity of media 10.

For example, specular light detector 12 includes an analog-to-digital converter and the indication of the intensity of light within specular reflectance component 14 is a digital indicator of intensity level. Alternatively, specular light detector 12 does not include an analog-to-digital converter and the indication of the intensity of light within specular reflectance component 14 is an analog indicator of intensity level.

Compare component 22 receives the indicator of the intensity of light and compares the indicator of the intensity of light with a mapping 21 of sensor output to media type to produce a media recognition output 23. For example, media recognition output 23 indicates a media type or indicates that there is no media detected.

For example, if the indication of the intensity of light within specular reflectance component 14 is an analog indicator of intensity, compare component 22 performs an analog-to-digital conversion before making the comparison. The mapping 21 of sensor output to media type can vary depending, for example, upon system configuration and expected media types.

Table 1 below shows an example mapping where expected media type includes blank transparency, blank white paper, blank plain paper, cyan colored plain paper, magenta colored plain paper, yellow colored plain paper and black colored plain paper:

TABLE 1

| Light Intensity | Media Type |
| --- | --- |
| 0-1 | No Media detected |
| 2 | Black colored plain paper |
| 3 | Yellow colored plain paper |

TABLE 1-continued

| Light Intensity | Media Type |
| --- | --- |
| 4 | Magenta colored plain paper |
| 5 | Cyan colored plain paper |
| 6 | Blank plain paper |
| 7 | Blank white paper |
| 8 | Blank transparency |

Table 1 can be derived for the media recognition system, for example, empirically by measuring light intensity for each expected media type and recording the result in mapping 21 of sensor output to media type.

The present invention allows detection of media types and the presence of media types using a single photo detector. The use of only a single photo detector results in a reduced material cost, a reduced process cost and reduced system complexity when implementing a media recognition system.

The forgoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

What is claimed is:

1. A media recognition system, comprising:
 a light source configured to generate a light beam;
 a light detector configured to detect a specular intensity of the light beam reflected from a media, the light detector being configured to generate an intensity indication representative of the detected specular intensity;
 a mapping component configured to store at least one stored media type indication; and
 a comparison component configured to compare the intensity indication to the at least one stored media type indication to determine a media type.

2. The media recognition system of claim 1, wherein the light source is a light-emitting diode.

3. The media recognition system of claim 1, wherein the light source is a blue light-emitting diode or a blue-violet light-emitting diode.

4. The media recognition system of claim 1, wherein the light detector is a photo diode.

5. The media recognition system of claim 1, wherein the mapping component includes a null stored media type indication configured to indicate that no media is present.

6. A method for detecting media type comprising:
 producing a light beam;
 detecting a specular reflectance of the light beam from a media; and
 comparing the specular reflectance to a mapping component to determine media type of the media;
 wherein the mapping component is configured to map the specular reflectance to a stored media type, the mapping component further being configured to utilize only the specular reflectance, and no other components of light, to map the specular reflectance to a media type representative of the media.

7. The method of claim 6, wherein the light beam is produced using a light-emitting diode.

8. The method of claim 6, wherein the light beam is produced using a blue light-emitting diode or a blue-violet light-emitting diode.

9. The method of claim 6, wherein the specular reflectance of the light beam is detected using a photo diode.

10. The method of claim 6, wherein the mapping component includes a null media type that indicates no media is present.

11. A media recognition system comprising:
 a light source configured to illuminate a media;
 a specular light detector configured to generate an intensity signal in response to a received specular intensity reflected from the media; and
 a comparison component configured to cross-reference the received specular intensity provided by the specular light detector to a mapping component having a plurality of media type specular reflectances stored therein;
 wherein the comparison component is configured to generate a media type output indicative of the media corresponding to the received specular intensity.

12. The media recognition system of claim 11, wherein the light source is a light-emitting diode.

13. The media recognition system of claim 12, wherein the light-emitting diode is a blue light-emitting diode or a blue-violet light-emitting diode.

14. The media recognition system of claim 11, wherein the specular light detector is a photo diode.

15. The media recognition system of claim 11, wherein the mapping component includes at least one of the plurality of media type specular reflectances indicating no media is present.

16. The media recognition system of claim 11, wherein the comparison component is configured to convert the received specular intensity indication from an analog indication to a digital indication.

17. A print system comprising:
 a print mechanism configured to deposit ink on a media; and
 a media recognition system in communication with the print mechanism;
 the media recognition system comprising:
 a light source arranged to illuminate the media;
 a specular light detector configured to generate an intensity signal representative of a detected specular reflectance received from the illuminated media; and
 a recognition map configured to cross-reference the intensity signal to a media type based on a comparison of the detected specular reflectance and a media type specular reflectance.

18. The print system of claim 17, wherein the print mechanism is selected from the group consisting of: a laser printer; an ink jet printer; a multi-function device or a facsimile machine.

19. The print system of claim 17, wherein the light source is a single light-emitting diode.

20. The print system of claim 19, wherein the light-emitting diode is a blue light-emitting diode or a blue-violet light-emitting diode.

21. The print system of claim 17, wherein the specular light detector is a photo diode.

22. The print system of claim 17, wherein the recognition map includes a value for the media type specular reflectance that corresponds to a no-media detected specular reflectance generated by the specular light detector.

23. A method for detecting media type comprising:
 configuring a print mechanism to deposit ink of a media;
 arranging a light source to illuminate the media;
 configuring a specular light detector to generate an intensity signal representative of a detected specular reflectance received from the illuminated media; and configuring a recognition map to cross-reference the intensity signal to a media type based on a comparison of the detected specular reflectance and a media type specular reflectance.

24. The method of claim 23 further comprising:
optimizing the print mechanism to deposit ink based on the media type.

25. The method of claim 23, wherein arranging the light source includes arranging a single light-emitting diode.

26. The method of claim 25, wherein the light emitting diode is a blue light-emitting diode or a blue-violet light-emitting diode.

27. The method of claim 23, wherein configuring the specular light detector includes configuring a photo diode.

28. A media recognition system comprising:
a printing system, the printing system comprising a processor and a memory, wherein the processor is configured to execute program logic stored on the memory, the program logic executable to control the printing system, and further executable to:

direct a light source upon a media;

detect a specular intensity indication reflected from the media in response to the light source;

compare the detected specular intensity indication to a mapping containing a plurality of media type specular reflectances; and generate a media type output indicative of the media represented by the detected specular intensity indication.

29. The media recognition system of claim 28, wherein the program logic is executable to generate a null value when the detected specular intensity indication indicates no media is present.

30. The media recognition system of claim 28, wherein the program logic is executable to convert the specular intensity indication from an analog indication to a digital indication.

* * * * *

UNITED STATES PATENT AND TRADEMARK OFFICE
CERTIFICATE OF CORRECTION

PATENT NO. : 7,429,744 B2  
APPLICATION NO. : 11/789555  
DATED : September 30, 2008  
INVENTOR(S) : Jiin Cheang Cheong et al.

Page 1 of 2

It is certified that error appears in the above-identified patent and that said Letters Patent is hereby corrected as shown below:

Column 4, Lines 37-38, Claim 17, delete
"17. A print system comprising:
a print mechanism configured to deposit ink on a media; and
a media recognition system in communication with the print mechanism;
the media recognition system comprising:
a light source arranged to illuminate the media;
a specular light detector configured to generate an intensity signal representative of a detected specular reflectance received from the illuminated media; and
a recognition map configured to cross-reference the intensity signal to a media type based on a comparison of the detected specular reflectance and a media type specular reflectance."

Column 4, Lines 37-38 insert
-- 17. A print system comprising:
a print mechanism configured to deposit ink on a media; and
a media recognition system in communication with the print mechanism;
the media recognition system comprising:
a light source arranged to illuminate the media;
a specular light detector configured to generate an intensity signal representative of a detected specular reflectance received from the illuminated media; and
a recognition map configured to cross-reference the intensity signal to a media type based on a comparison of the detected specular reflectance and a media type specular reflectance. --;

Signed and Sealed this  
Fourth Day of January, 2011

David J. Kappos  
*Director of the United States Patent and Trademark Office*

Column 4, Line 63, Claim 23, delete "of" and insert -- on --;

Column 5, Line 10, Claim 26, delete "light emitting" and insert -- light-emitting --.